(12) United States Patent
Masini

(10) Patent No.: US 6,500,179 B1
(45) Date of Patent: Dec. 31, 2002

(54) BONE CUTTING GUIDE AND METHOD TO ACCOMMODATE DIFFERENT-SIZED IMPLANTS

(75) Inventor: Michael A. Masini, Ann Arbor, MI (US)

(73) Assignee: MedIdea, LLC, Ann Arbor, MI (US)

( * ) Notice: Subject to any disclaimer, the term of this patent is extended or adjusted under 35 U.S.C. 154(b) by 358 days.

(21) Appl. No.: 09/342,439

(22) Filed: Jun. 29, 1999

Related U.S. Application Data

(63) Continuation of application No. 09/017,509, filed on Feb. 2, 1998, now Pat. No. 5,916,220.

(51) Int. Cl.$^7$ .............................................. A61B 17/56
(52) U.S. Cl. ........................................ 606/88; 606/102
(58) Field of Search ............................. 606/88, 82, 86, 606/87, 89, 102, 79, 80; 623/20

(56) References Cited

U.S. PATENT DOCUMENTS

| | | | |
|---|---|---|---|
| 5,258,032 A | 11/1993 | Bertin | 623/20 |
| 5,474,559 A | 12/1995 | Bertin et al. | 606/89 |
| 5,486,178 A | 1/1996 | Hodge | 606/82 |
| 5,593,411 A | 1/1997 | Stalcup et al. | 606/88 |
| 5,601,563 A | 2/1997 | Burke et al. | 606/86 |
| 5,613,969 A | 3/1997 | Jenkins, Jr. | 606/87 |
| 5,624,444 A | 4/1997 | Wixon | 606/88 |
| 5,653,714 A | 8/1997 | Dietz et al. | 606/87 |
| 5,662,656 A | 9/1997 | White | 606/88 |
| 5,925,049 A | * 7/1999 | Gustilo et al. | 606/82 |

FOREIGN PATENT DOCUMENTS

| | | |
|---|---|---|
| EP | 380451 | 8/1990 |
| EP | 466659 | 1/1992 |

* cited by examiner

*Primary Examiner*—Michael H. Thaler
(74) *Attorney, Agent, or Firm*—Gifford, Krass, Groh, Sprinkle, Anderson & Citkowski, PC

(57) ABSTRACT

A bone-modification device includes a plurality of cutting guides, wherein at least one of the guides is used to resect or otherwise modify a bone to receive a prosthetic element of a particular size, and one or more additional guides to modify or resect the bone in conjunction with a prosthetic element of a different size. In one disclosed example, the guides are configured to resect a distal femur so as to receive a femoral prosthesis in conjunction with knee-replacement surgery, wherein a plurality of guide sets are provided for anterior, posterior, and associated chamfer cuts for a plurality of differently sized femoral prosthesis. In this instance, the guide preferably features one or more sets of spaced-apart saw-receiving slots, including a first slot to resect the bone to receive a femoral prosthesis of a first size, and a second slot to resect the bone to receive a femoral prosthesis of a second size, different from the first.

28 Claims, 3 Drawing Sheets

BONE CUTTING GUIDE AND METHOD TO ACCOMMODATE DIFFERENT-SIZED IMPLANTS

This application is a continuation of application Ser. No. 09/017,509, filed Feb. 2, 1998 now U.S. Pat. No. 5,916,220.

FIELD OF THE INVENTION

This invention relates generally to orthopaedics and, in particular, to apparatus and methods of use enabling multiple bone resections to be performed for different-sized implants using a common fixture.

BACKGROUND OF THE INVENTION

Prosthetic joint components are being installed with increasing frequency due to the enhanced stability and longevity of improved implants and surgical techniques. As a consequence, younger patients are electing joint-replacement surgery to enhance movement or alleviate pain.

In many joint-replacement situations, it is common practice to use bone-cutting guides to perform resections that correspond to the surfaces of a final implant used for fixation. In the case of primary knee-replacement surgery, for example, a stem is introduced into the distal femoral intramedullary canal to which various measurement and cutting appliances are attached.

Typically, a distal cutting guide is first installed on the stem, which is used to create a flat surface on the very end of the bone. A sizing jig is then attached in contact with this surface. Such jigs typically include adjustable feelers which touch the bone anteriorly and posteriorly, enabling the surgeon to obtain a visual indication of the correct-size implant for the patient's physiology.

Having determined the appropriate size, pins (or drill holes) are introduced into the end of the bone, and a cutting guide specifically adapted for a particular size of implant is fitted onto the pins, enabling the anterior, posterior and chamfer cuts to be performed. Typically, the location of the pins also takes into account the degree of joint rotation required, which is on the order of three degrees of external rotation for knee-replacement surgery.

Although the system just described functions adequately in most cases, it does present certain drawbacks which tend to consume time and compromise accuracy.

SUMMARY OF THE INVENTION

Broadly and in general terms, this invention provides a device incorporating a plurality of cutting guides, wherein at least one of the guides is used to resect or otherwise modify a bone to receive a prosthetic element of a particular size, and one or more additional guides to modify or resect the bone in conjunction with a prosthetic element of a different size. Although the specification and drawings focus on primary total knee arthroplasty, it will be apparent to one of skill in the art of orthopaedic surgery that the inventive principles disclosed here are equally applicable to other joints and bone-modification situations that might benefit from apparatus and methods enabling multiple bone resections to be performed for different-sized implants using a common fixture.

A device for cutting a bone to receive one of a plurality of differently sized prosthetic elements according to the invention comprises a body having a plurality of bone-cutting guides, including a first guide associated with cutting the bone to receive one of the prosthetic elements, and a second guide associated with cutting the bone to receive a different one of the prosthetic elements. In the preferred embodiment the guides take the form of parallel, spaced-apart slots extending through at least a portion of the body, though alternative guides may be provided for different cutting tools such as osteotomes and routers.

In a preferred embodiment, the device further includes a fixture enabling the body to be moved relative to bone to assist the practitioner in determining which of the prosthetic elements and associated guide should be used to resect the bone. The fixture may further include one or more bone-measurement gauges to provide additional assistance in determining which of the prosthetic elements and associated guides should be used. The various guides may also be oriented relative to the body and/or its direction of movement to account for external joint rotation.

Where the bone-cutting guides are configured to resect a distal femur so as to receive a femoral prosthesis in conjunction with knee-replacement surgery, a plurality of guide sets may be provided for anterior, posterior, and associated chamfer cuts for a plurality of differently sized femoral prosthesis. In this case, the body will preferably feature one or more sets of spaced-apart saw-receiving slots, including a first slot to resect the bone to receive a femoral prosthesis of a first size, and a second slot to resect the bone to receive a femoral prosthesis of a second size, different from the first.

DETAILED DESCRIPTION OF THE INVENTION

Figure 1:
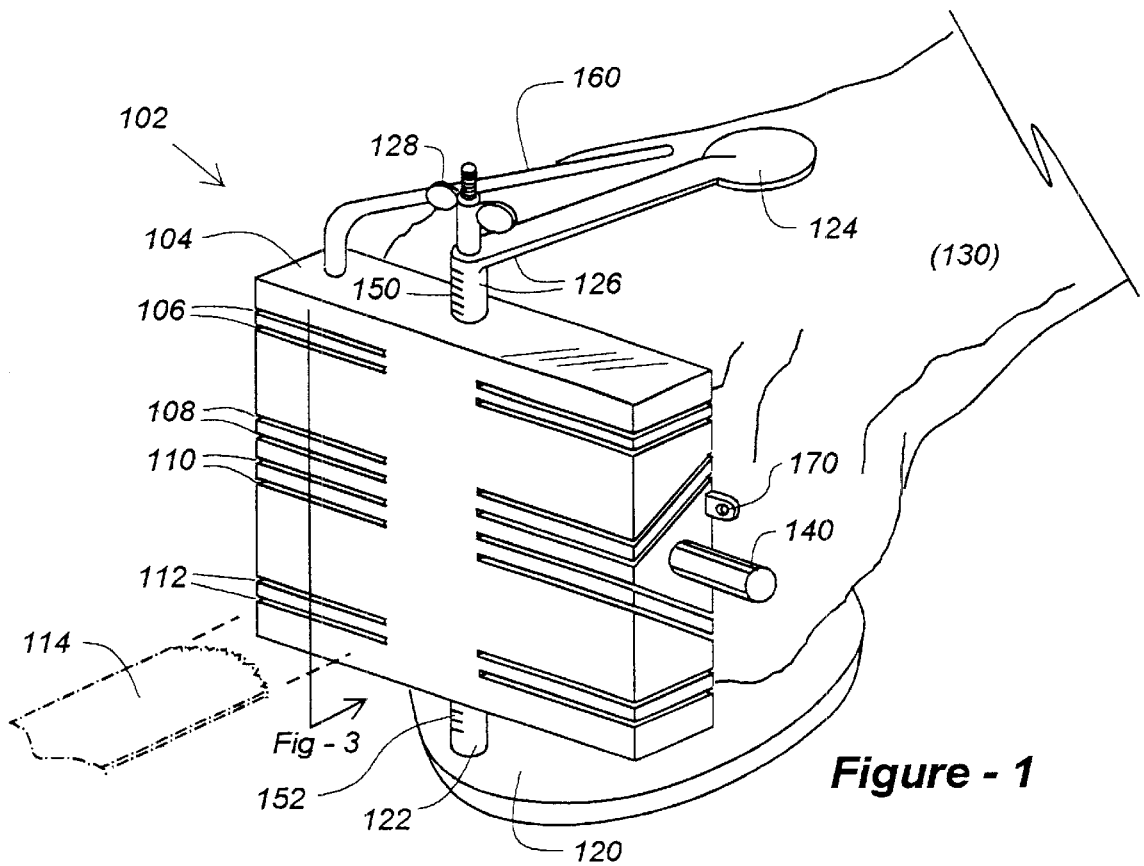
FIG. 1 illustrates from an oblique perspective a cutting guide according to the invention which can accommodate two differently sized femoral prosthetic elements, along with a mechanism and fine control for moving the guide relative to a distal femur prior to resection.

FIG. 1 depicts generally at 102 instrumentation according to the invention applicable to primary total knee arthroplasty. Broadly, the apparatus includes a body having a plurality of cutting guides, wherein at least one of the guides is used to resect or otherwise modify a bone to receive a prosthetic element of a particular size, and one or more additional guides to modify or resect the bone in conjunction with a prosthetic element of a different size. A mechanism is also disclosed to move the body relative to the bone and fastened into place to perform the desired cuts.

In a preferred embodiment, the body assumes the form of a cutting block 104 as shown in FIG. 1, and the guides take the form of slots such as sets 106, 108, 110 and 112, which are sized to receive a commercially available oscillating flat saw blade 114. Although in this example slots are depicted, the invention is equally applicable to alternative cutting tools and guides therefore, including osteotomes, routers, and so forth.

In the embodiment of FIG. 1, slot set 106 is used to perform anterior cuts for two differently sized prosthetic elements; set 108 is used for anterior chamfer cuts; set 112 for posterior cuts; and set 110 for posterior chamfer cuts. Fewer guides may be provided for use in situations wherein there are fewer resections to be performed for a given implant, and more guides may be used, for example, to accommodate three or more differently sized implants.

The device 102 optionally further includes a posterior gauge 120 coupled to a member 122, and an anterior gauge 124 coupled to a member 126. As perhaps best understood with reference to FIG. 2, the members 122 and 126 preferably interlock within the body of the block 104, with a manually operated fastener 128 being used to compress the gauges while compressively urged against respective protrusions of a bone 130. Such interlocking enables the cutting guide to be moved in an anterior or posterior direction against a previously prepared distal bone surface, permitting resections for more than one size prosthesis to be performed using the same apparatus, while enabling fine adjustments to be made between the guide and the bone for any given size of implant.

Figure 3:
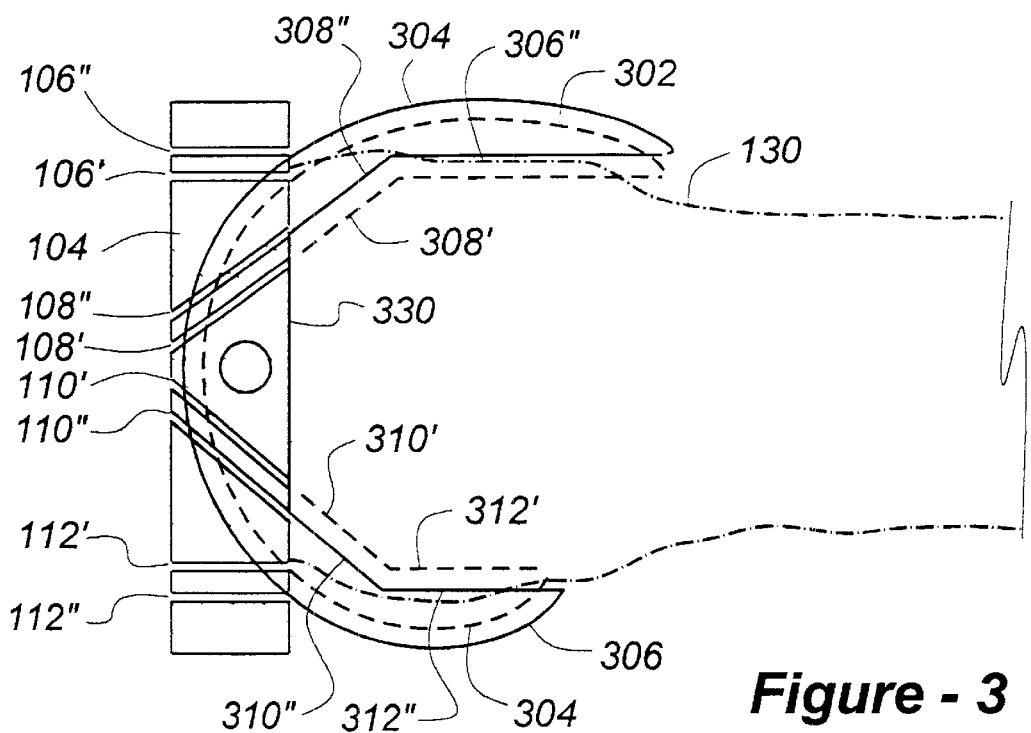
FIG. 3 is a side-view drawing taken in cross-section with respect to the section plane illustrated in FIG. 1.

Now making particular reference to FIG. 3, slots 106', 108', 110' and 112" might correspond to a size 2 femoral implant 202 depicted in broken-line form, whereas slots 106", 108", 110" and 112" might correspond to a size 3 implant 204. That is, slot 106' would be used to create a resected surface 306' to receive a corresponding surface on implant 302, slot 108' would be used to create surface 308'; slot 110' for surface 310', and slot 112'for surface 312'. At the same time, slot 106 " could be used to create a surface corresponding to the surface 306" of implant 304, slot 108" corresponding to surface 308", slot 110" to surface 310", and slot 112" to surface 312".

Although the device 104 could be used to perform resections for either sized prosthetic element shown in the drawing, by viewing the portions of FIG. 3 in cross-section, it is noted that the profile of bone 130 is sufficiently compact that the implant designated 302 should suffice in this particular case, thereby enabling the primed (as opposed to double-primed) guides to be utilized for a correct fit.

The guide block preferably features a smooth, planar backside 330, enabling the device to be positioned against a previously prepared surface such as a resected distal surface. The surgeon then slides the. device anteriorly and posteriorly to determine the most appropriate size, even when otherwise close to being between sizes. Upon arriving at a desired position, the device may be fastened into place using pins though holes 170 or other suitable temporary fixation means, and the various resections performed, as required.

Figure 2:
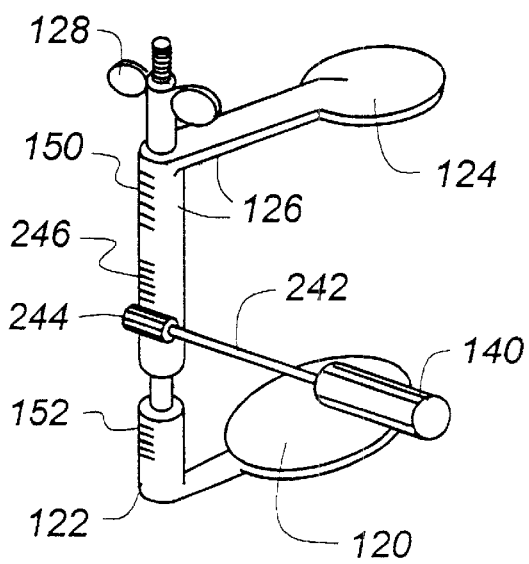
FIG. 2 is an oblique representation. of aspects of the internal fine-control mechanism shown in FIG. 1.

To assist in positioning, subtle adjustments may be achieved by moving the guide body with a fine control knob 140 which, as shown in FIG. 2, couples to a rod 242 and toothed element 244. The element 244, in turn, interacts with teeth 246 to move the entire block and down relative to the bone when held in place by gauges 120 and 124 upon being tightened using fastener 128. This action facilitates adjustment of the block slightly anteriorly if, for example, the surgeon feels it would be most appropriate to lower the implant size while not wishing to notch the anterior femur. Readouts 150 and 152 may be provided for a visual indication of element size selection, and/or one or more additional "feeler gauges" such as element 160 may be used to make contact with an appropriate portion of the bone indicative of a particular implant size.

Procedurally, the surgeon might look at the position of the block 104, or the readouts 150 and 152, or the gauges, or all of the above to determine correct sizing. In the event that a larger size is indicated by viewing the bottom of the block and the way in which the posterior guides correlate to the bone to be resected, the surgeon might decide that the result would require too large an implant if installed. The fine control aspect of the invention may then be used to move the guide relative to the bone to ensure that bone removal and/or implant size are optimized for a given patient physiology. To avoid notching the anterior femur with the smaller size, the guide may be moved until both position and size are visually evident, at which time the body may be temporarily anchored and all of the desired resections performed.

Figure 4:
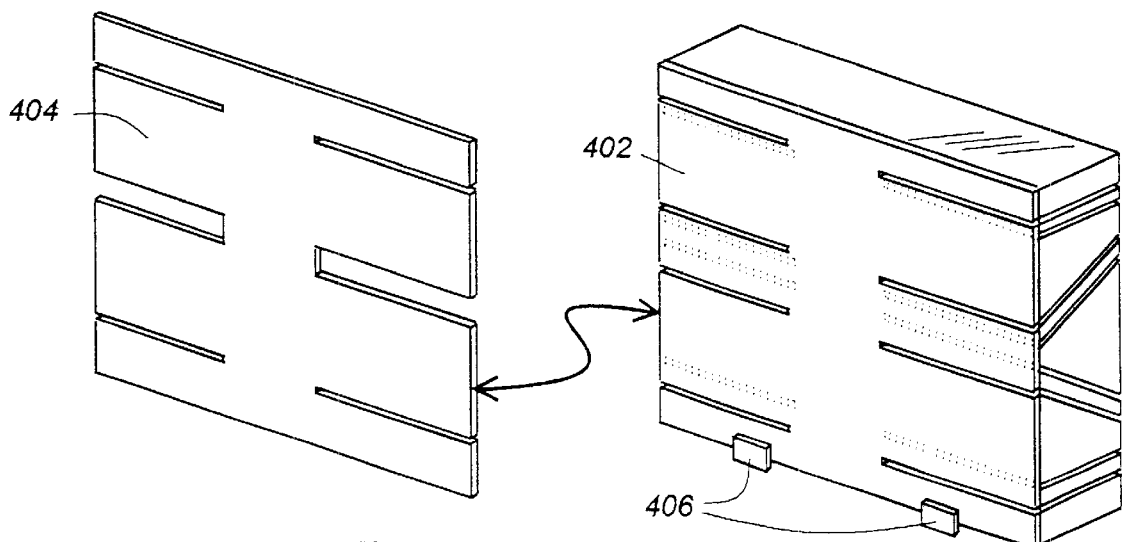
FIG. 4 is an oblique drawing which shows how templates may be placed over a cutting guide to ensure that only the correct guides are used for a particular size of implant.

To avoid making mistakes, templates may be provided as shown in FIG. 4, with a first template 402 being used for one set of slots and a second template 404 being employed for another set of slots corresponding to a differently sized implant. Clips 406 or other form of appropriate retaining mechanism may be used to hold the such templates against the guide, as required. In addition, the guide block may be provided with colors; red, for example, might indicate a size 2; green for size 3, and so forth, and the surgeon would know to rely on the same color for a particular size.

Figure 5:
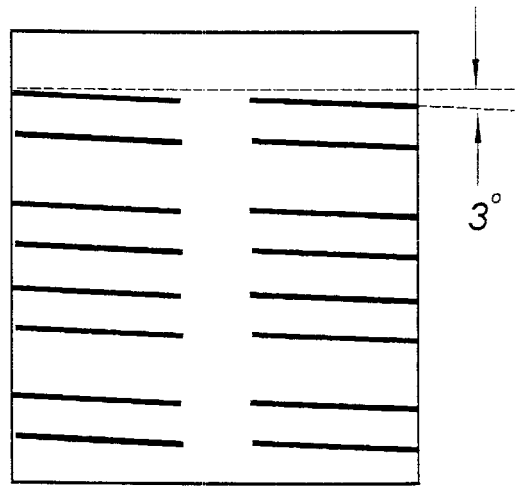
FIG. 5 illustrates how, in a preferred embodiment of the invention, slots or cutting guides may be angled to account for external rotation, for example, in knee replacement surgery.

Making reference to FIG. 5, in the case of knee arthroplasty, a few degrees (i.e., 3 degrees) of external rotation are usually provided with respect to the femoral component. To accomplish this, a desired amount of external rotation may be added to the planes of the guide surfaces relative to the body of the cutting block, as shown in the Figure. Indeed, if the cutting body is symmetrical about a pivotal axis, the body may be turn around to accommodate the appropriate rotation for the right and left legs without the need for an additional piece of instrumentation.

Figure 6:
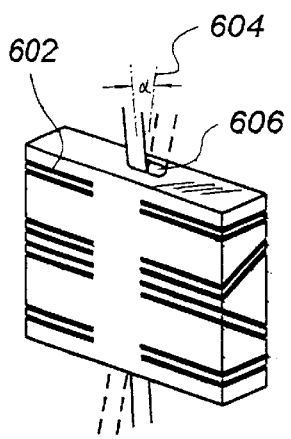
FIG. 6 illustrates an alternative approach to accommodating external rotation through tilting of the guide itself relative to its anterior-posterior axis.

FIG. 6 illustrates an alternative to providing guides or slots at an angle relative to the body of the guide as shown in FIG. 5. In the case of FIG. 6, the slot openings 602 (or alternative cutting guides) are substantially transverse to the axis 604 of the cutting block, but an elongated slot 606 is provided at the top and bottom of the device, enabling the entire block to be turned slightly clockwise or counterclockwise and locked into place, for example, at a desired angle of external rotation for both the right and left knees of the patient.

Figure 7:
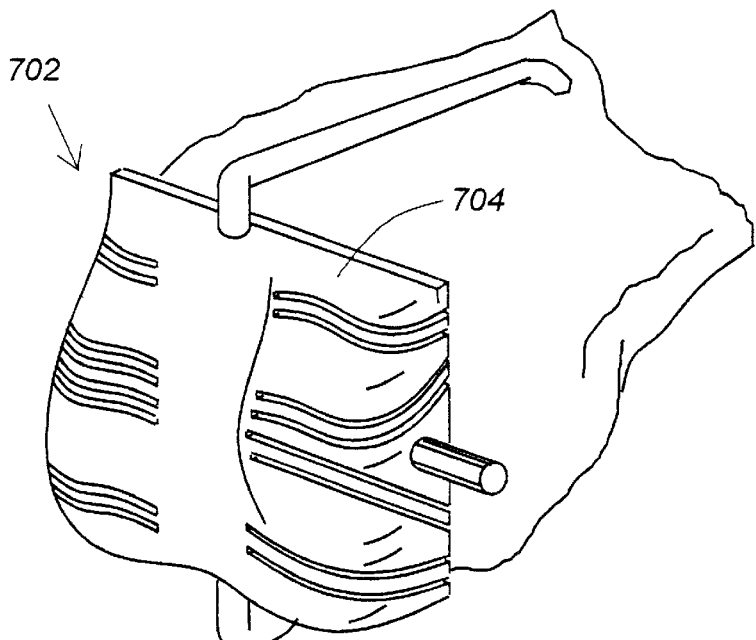
FIG. 7 illustrates, from an oblique perspective, an alternative embodiment of the invention wherein a cutting block according to the invention includes outer surfaces configured to co-act in a joint.

FIG. 7 illustrates, from an oblique perspective generally at 702, an alternative embodiment of the invention wherein the body of a cutting guide 704 includes an outer surface which is shaped to co-act in a joint. A particular manifestation illustrated in FIG. 7 is that of a distal femur, wherein the outer surfaces contain condylar protrusions enabling the device to be reduced into a joint and adjusted as part of a joint reduction to observe and establish correct joint activity. Preferably, the fixture used to hold the cutting guide relative to the bone to be modified is also sufficiently low in profile that the assembly may be reduced for joint testing purposes.

Figure 8:
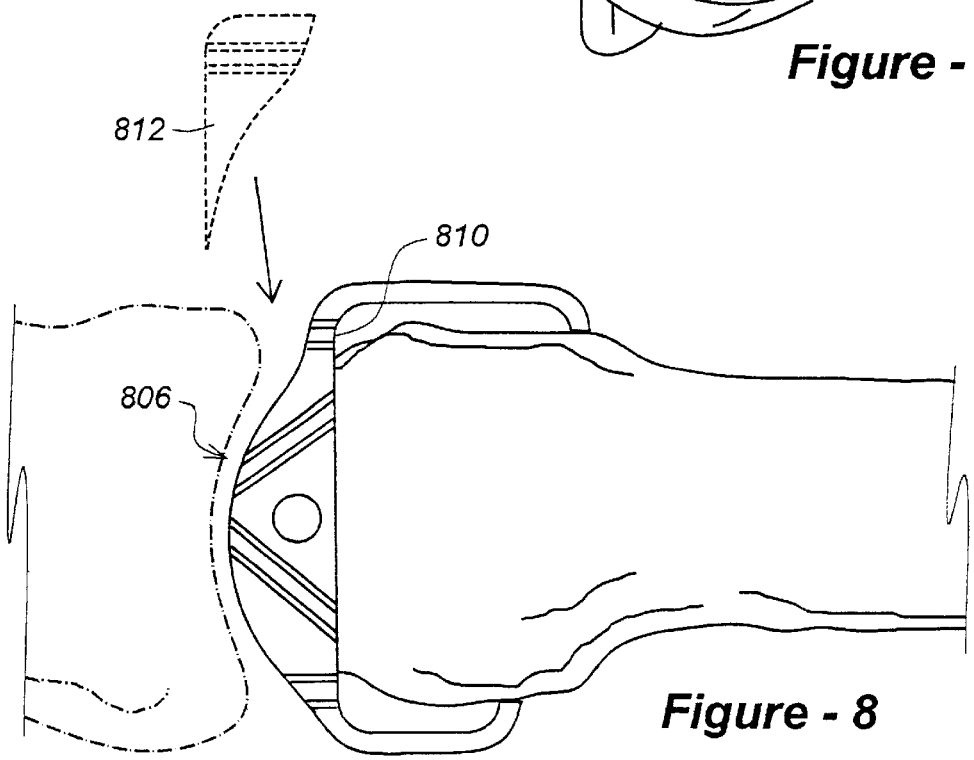
FIG. 8 is a side-view cross-section of the alternative embodiment depicted in FIG. 7.

FIG. 8 illustrates in cross section the alternative embodiment of FIG. 7 wherein the condylar surfaces are able to interact with an opposing proximal tibial surface 806 as part of a trial reduction. Upon achieving an acceptable level of cooperation within the joint, the joint may be exposed and the required resections performed using the slots or guides provided. The positioning of the guide in this case may either be locked into place before, during or after the trial reduction process, depending upon the means used for temporary fixation to make the various bone cuts. In the event that the outer shape thins a guide-containing region as in the vicinity of slots 810, a guide/slot lengthener component 812 may me temporarily installed for resection following reduction.

I claim:

1. A device for cutting a bone to receive one of a plurality of differently sized prosthetic elements, the device comprising:

a body having a plurality of bone-cutting guides, including an anterior and a posterior guide associated with cutting the bone to receive one of the prosthetic elements, and a second anterior or posterior guide associated with cutting the bone to receive a different one of the prosthetic elements; and wherein the bone-cutting guides are slanted to account for rotation of the prosthetic element relative to the bone.

2. The device of claim 1, wherein the guides are in the form of parallel, spaced-apart slots extending through at least a portion of the body.

3. The device of claim 1, further including a fixture enabling the body to be moved relative to bone to assist the user in determining which of the prosthetic elements, and associated guides, should be used to cut the bone.

4. The device of claim 1, wherein the fixture further includes one or more bone-measurement gauges to assist the user in determining which of the prosthetic elements, and associated guides, should be used to cut the bone.

5. The device of claim 1, wherein the bone-cutting guides are configured to resect a distal femur to receive a femoral prosthesis in conjunction with knee-replacement surgery.

6. The device of claim 1, wherein the body includes a shaped outer surface adapted to co-act within a joint as part of a trial reduction.

7. A device for resecting a distal femur to receive one of a plurality of differently sized femoral prostheses as part of a knee-replacement surgery, the device comprising:

a body having one or more sets of spaced-apart saw-receiving slots, including at least one anterior slot and at least one posterior slot to resect the bone to receive a femoral prosthesis of a given size, and a fixture enabling the body to be moved along a line oriented substantially anterior to posterior; and wherein the angle formed by the slots and the line are perpendicular but for a few degrees to account for joint rotation.

8. The device of claim 7, including a set of slots associated with performing a chamfer cut.

9. The device of claim 7, including at least one slot associated with performing an anterior cut for an implant of a different size.

10. The device of claim 9, wherein the device further includes one or more bone-measurement gauges to assist in the determination of which prosthesis and associated guide should be used for resection as the body is moved relative to the femur.

11. The device of claim 7, including at least one slot associated with performing a posterior cut for an implant of a different size.

12. The device of claim 11, wherein the device further includes one or more bone measurement gauges to assist in the determination of which prosthesis and associated guide should be used for resection as the body is moved relative to the femur.

13. The device of claim 7, wherein the body includes a substantially planar back surface adapted for placement against a previously prepared distal surface.

14. The device of claim 7 wherein the body includes an outer surface with condylar protrusions to facilitate a trial knee joint reduction.

15. A device for cutting a bone to receive one of a plurality of differently sized prosthetic elements, the device comprising:

a body having a plurality of bone-cutting guides, including an anterior and a posterior guide associated with cutting the bone to receive one of the prosthetic elements, and a second anterior or posterior guide associated with cutting the bone to receive a different one of the prosthetic elements;

wherein the body includes a shaped outer surface adapted to co-act within a joint as part of a trial reduction.

16. The device of claim 15, wherein the guides are in the form of parallel, spaced-apart slots extending through at least a portion of the body.

17. The device of claim 15, further including a fixture enabling the body to be moved relative to bone to assist the user in determining which of the prosthetic elements, and associated guides, should be used to cut the bone.

18. The device of claim 15, wherein the fixture further includes one or more bone-measurement gauges to assist the user in determining which of the prosthetic elements, and associated guides, should be used to cut the bone.

19. The device of claim 15, wherein the bone-cutting guides are slanted to account for rotation of the prosthetic element relative to the bone.

20. The device of claim 15, wherein the bone-cutting guides are configured to resect a distal femur to receive a femoral prosthesis in conjunction with knee-replacement surgery.

21. A device for resecting a distal femur to receive one of a plurality of differently sized femoral prostheses as part of a knee-replacement surgery, the device comprising:

a body having one or more sets of spaced-apart saw-receiving slots, including at least one anterior slot and at least one posterior slot to resect the bone to receive a femoral prosthesis of a given size, and a fixture enabling the body to be moved along a line oriented substantially anterior to posterior;

wherein the body includes an outer surface with condylar protrusions to facilitate a trial knee joint reduction.

22. The device of claim 21, including a set of slots associated with performing a chamfer cut.

23. The device of claim 21, including at least one slot associated with performing an anterior cut for an implant of a different size.

24. The device of claim 23, wherein the device further includes one or more bone-measurement gauges to assist in the determination of which prosthesis add associated guide should be used for resection as the body is moved relative to the femur.

25. The device of claim 21, including at least one slot associated with performing a posterior cut for an implant of a different size.

26. The device of claim 25, wherein the device further includes one or more bone-measurement gauges to assist in the determination of which prosthesis and associated guide should be used for resection as the body is moved relative to the femur.

27. The device of claim 21, wherein the angle formed by the slots and the line are perpendicular except for a few degrees to account for joint rotation.

28. The device of claim 21, wherein the body includes a substantially planar back surface adapted for placement against a previously prepared distal surface.

* * * * *